United States Patent
Turos et al.

(10) Patent No.: US 8,404,671 B2
(45) Date of Patent: *Mar. 26, 2013

(54) HETEROSUBSTITUTED N-THIOLATED BETA-LACTAM COMPOUNDS AND METHODS OF USE

(75) Inventors: Edward Turos, Wesley Chapel, FL (US); Praveen Ramaraju, Tampa, FL (US)

(73) Assignee: University of South Florida, Tampa, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 12/951,778

(22) Filed: Nov. 22, 2010

(65) Prior Publication Data

US 2011/0160178 A1   Jun. 30, 2011

Related U.S. Application Data

(63) Continuation of application No. 11/852,100, filed on Sep. 7, 2007, now Pat. No. 7,846,920.

(60) Provisional application No. 60/844,291, filed on Sep. 13, 2006.

(51) Int. Cl.
| | |
|---|---|
| C07D 205/08 | (2006.01) |
| C07D 227/087 | (2006.01) |
| A61K 31/397 | (2006.01) |
| A61K 31/4035 | (2006.01) |
| A61P 31/04 | (2006.01) |

(52) U.S. Cl. .................. 514/210.15; 540/355
(58) Field of Classification Search .................. 540/355; 514/210.15
See application file for complete search history.

(56) References Cited

U.S. PATENT DOCUMENTS

| | | |
|---|---|---|
| 3,838,114 A | 9/1974 | Lawrence |
| 6,375,926 B1 | 4/2002 | Barnes |
| 6,476,015 B1 | 11/2002 | Turos et al. |
| 6,946,458 B2 | 9/2005 | Turos |
| 2004/0167115 A1 | 8/2004 | Dou et al. |
| 2007/0265243 A1 | 11/2007 | Turos |

OTHER PUBLICATIONS

Heldreth, B., Long, T.E., Jang, S., Reddy, G.S.K., Turos, E., Dickey, S., and Lim, D.V., "N-Thiolated b-lactam antibacterials: Effects of the N-organothio substituent on anti-MRSA activity" *Bioorganic & Medicinal Chemistry* 2006, pp. 3775-3784, vol. 14.
Kalnins, M.,"Reactions of Phthalimide and Potassium Phthalimide with Sulfur Monochloride," *Canadian Journal of Chemistry*,1966, pp. 2111-2113 vol. 44.
Ren et al. "Studies on Nonconventionally Fused Bicyclic β-Lactams" *J. Org. Chem.*, 1998 pp. 8898-8917, vol. 63.
Revell, K.D., Heldreth, B., Long, T.E., Jang, S., and Turos, E., "N-thiolated b-lactams: Studies on the mode of action and identification of a primary cellular target in *Staphylococcus aureus*" *Bioorganic & Medicinal Chemistry*, 2007, pp. 2453-2467 vol. 15.
Turos, E., Konaklieva, M.I., Ren, R.X-F., Shi, H., Gonzalez, J., Dickey, S., and Lim, D.V., "N-Thiolated Bicyclic and Monocyclic b-Lactams" *Tetrahedron*, 2000, pp. 5571-5578, vol. 56.
Turos, E., Long, T.E., Heldreth, B., Leslie, J.M., Reddy, G.S.K., Wang, Y., Coates, C., Konaklieva, M., Dickey, S., Lim, D.V., Alonso, E., and Gonzalez J., "N-Thiolated b-lactams: A new family of anti-Bacillus agents" *Bioorganic & Medicinal Chemistry Letters*, 2006, pp. 2084-2090, vol. 16.
Turos, E., Shim, J., Wang, Y., Greenhalgh, K., Reddy, G.S.K., Dickey, S., and Lim, D.V., "Antibiotic-conjugated polyacrylate nanoparticles: New opportunities for development of anti-MRSA agents" *Bioorganic & Medicinal Chemistry Letters*, 2007, pp. 53-56, vol. 17.
Burnett, D.A. et al. "β-lactams from esters and sulfenimines: A new route to monobactams" *J. Org. Chem.*, 1986, 51:1929-1930.
Turos, E. et al. "*N*-methylthio β-lactam antibacterials: Effects of the $C_3/C_4$ ring substituents on anti-MRSA activity" *Bioorganic & Medicinal Chem.*, 2005, 13:6289-6308.

*Primary Examiner* — Mark Berch
(74) *Attorney, Agent, or Firm* — Saliwanchik, Lloyd & Eisenschenk

(57) ABSTRACT

The invention relates to heterosubstituted N-thiolated beta-lactams, compositions comprising these compounds, methods for their production, and methods of use as antibiotics to inhibit the growth of bacteria. In one embodiment, the compounds have the structure shown in formula (A) or formula (B) or formula (C):

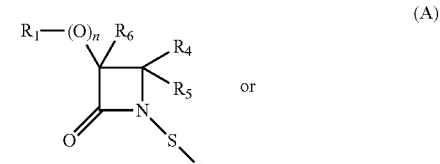

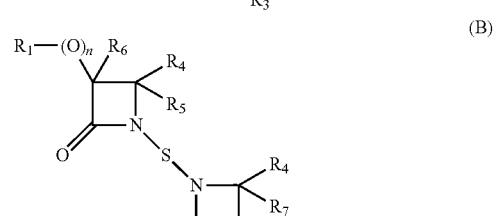

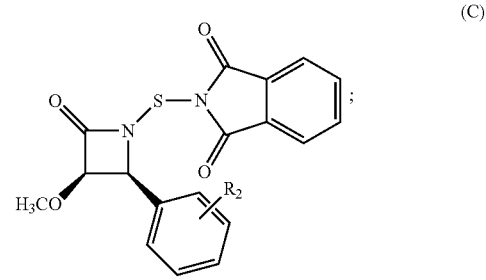

wherein the R groups are as defined in the specification. The antibacterial agents of the invention can be administered to a human or animal to treat or inhibit bacterial infection, such as that of *Staphylococcus* species, including methicillin-resistant *Staphylococcus aureus* (MRSA).

45 Claims, 6 Drawing Sheets

$\xrightarrow{S_2Cl_2 \quad DMF}_{0°C - rt}$  (I)

(X)

(Y)

HETEROSUBSTITUTED N-THIOLATED BETA-LACTAM COMPOUNDS AND METHODS OF USE

CROSS-REFERENCE TO RELATED APPLICATIONS

The present application is a continuation of U.S. application Ser. No. 11/852,100, filed Sep. 7, 2007, which claims the benefit of U.S. Provisional Application Ser. No. 60/844,291, filed Sep. 13, 2006, each of which is hereby incorporated by reference herein in its entirety, including any figures, tables, nucleic acid sequences, amino acid sequences, and drawings.

GOVERNMENT SUPPORT

This invention was made with government support under grant number RO1 AI051351 awarded by the National Institutes of Health. The government has certain rights in the invention.

BACKGROUND OF THE INVENTION

For more than 60 years, N-thiolated β-lactam antibiotics have played an essential role in treating bacterial infections (Morin et al., 1982 and Kukacs et al., 1990). The development of multi-drug resistant *Staphylococcus* infections is an increasing concern for the global health community. Infection caused by methicillin-resistant *Staphylococcus aureus* (MRSA) is becoming increasingly difficult to treat with conventional antibiotics, leading to a sharp rise in clinical complications. Recently a new class of N-thiolated β-lactam has been found to inhibit bacterial growth in *Staphylococcus aureus* (Turos et al., 2000) including methicillin-resistant *Staphylococcus aureus* (MRSA) strains.

BRIEF SUMMARY OF THE INVENTION

The present invention concerns heterosubstituted N-thiolated beta-lactam compounds, compositions comprising these compounds, methods for their production, and methods of use as antibiotics to inhibit the growth of bacteria. The antibacterial agents of the invention can be administered to a human or animal to treat or inhibit bacterial infection (therapeutically or prophylactically), such as that of *Staphylococcus* species, including methicillin-resistant *S. aureus*.

BRIEF DESCRIPTION OF THE DRAWINGS

FIG. 4A is structure X, FIG. 4B is structure Y, and FIG. 4C is structure Z.

DETAILED DESCRIPTION OF THE INVENTION

Figure 1:
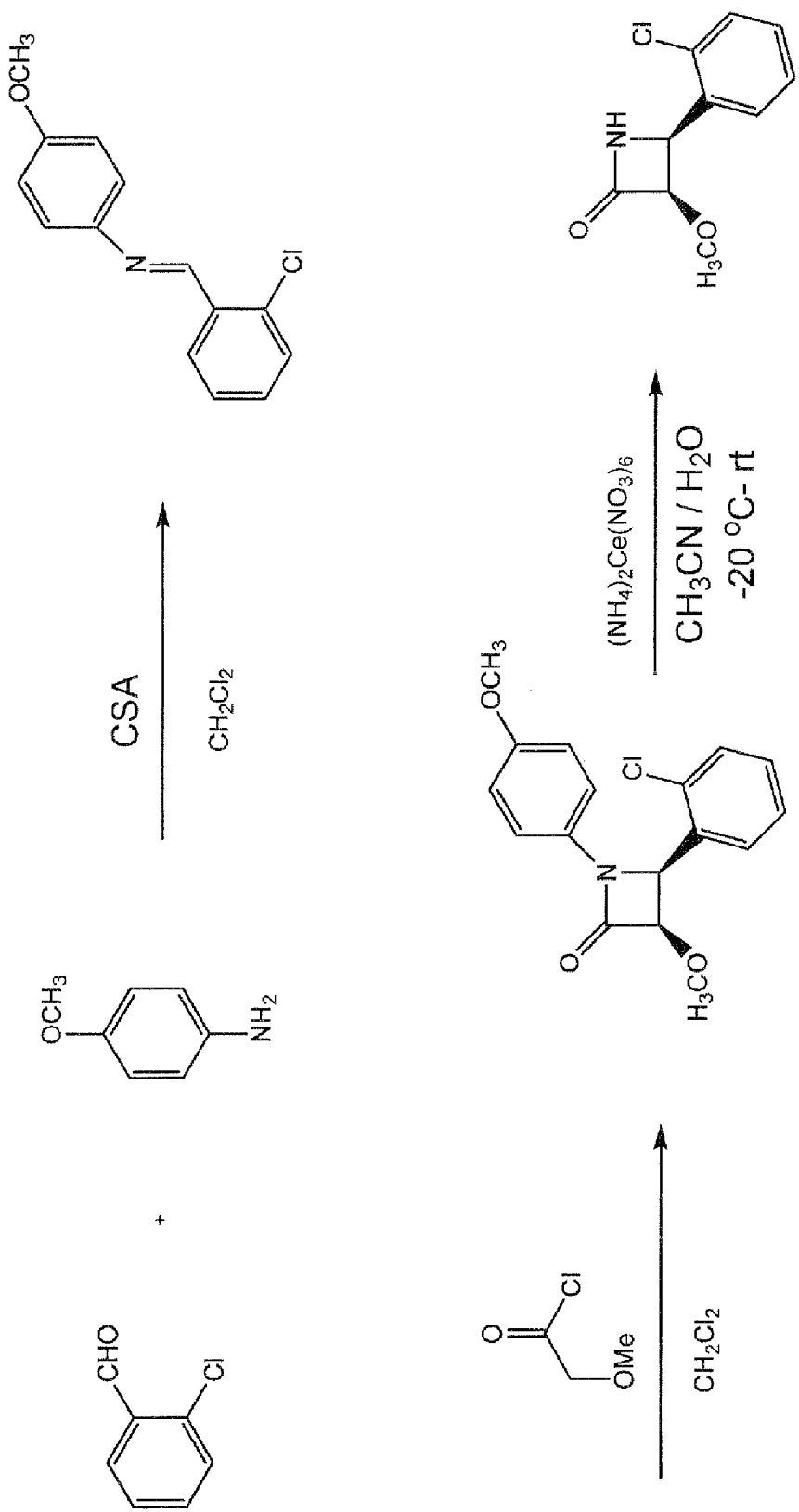
FIG. 1 shows a reaction scheme for the synthesis of beta-lactams that can be used according to the present invention (see Turos et al. (2005)).
Figure 2:
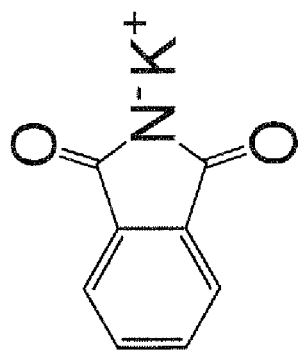
FIG. 2 shows a reaction scheme for the synthesis of a phthalimide dimer that can be used according to the present invention (see Kalnins (1966)).
Figure 2:
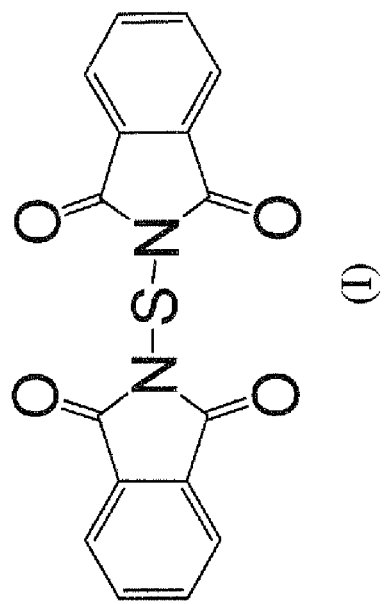

The present invention concerns heterosubstituted N-thiolated beta-lactams. In one embodiment, a beta-lactam compound of the invention has the structure shown in formula (A):

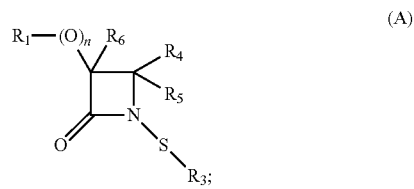

(A)

wherein $R_1$ is a hydrocarbon group having 1 to 8 carbon atoms and can be, for example, an alkyl, alkenyl, or alkynyl group;

$R_3$ is a heteroalkyl, heterocycloalkyl or heteroaryl, any of which can be optionally substituted with $R_2$, wherein $R_2$ is one or more halides, hydroxyl, nitro, cyano, alkyl, alkenyl, alkynyl, aryl, heteroaryl, cycloalkyl, heterocycloalkyl, cycloalkenyl, heterocycloalkenyl, alkoxy, amido, amino, carboxylic ester group, —CHO, —COOH, or COX, wherein X is Cl, F, Br, or I;

$R_4$, $R_5$, and $R_6$ are, independently, hydrogen, alkyl, alkenyl, alkynyl, aryl, heteroalkyl, heteroaryl, cycloalkyl, heterocycloalkyl, cycloalkenyl, heterocycloalkenyl, halides, hydroxyl, nitro, cyano, alkoxy, amido, amino, carboxylic ester group, —CHO, —COOH, or COX, wherein X is Cl, F, Br, or I; any of which can be optionally substituted with $R_2$, wherein $R_2$ is one or more halides, hydroxyl, nitro, cyano, alkyl, alkenyl, alkynyl, aryl, heteroaryl, cycloalkyl, heterocycloalkyl, cycloalkenyl, heterocycloalkenyl, alkoxy, amido, amino, carboxylic ester group, —CHO, —COOH, or COX, wherein X is Cl, F, Br, or I; and wherein n=0 or 1;

or a pharmaceutically acceptable salt, hydrate, ester or amide thereof.

In one embodiment, a compound of the invention has the structure shown in formula (A) wherein $R_1$ is an alkyl group. In another embodiment, $R_4$ is an aryl group. In a specific embodiment, $R_1$ is an alkyl group and $R_4$ is an aryl group. In an exemplified embodiment, $R_1$ is a methyl and $R_4$ is phenyl optionally substituted with one or more halogens. In a specific embodiment, the halogen is Cl or Br. In a specific embodiment, $R_3$ is attached to the sulfur atom through a heteroatom, such as an N atom. In one embodiment, $R_3$ is an optionally substituted phthalimido. In one embodiment, a compound has the structure:

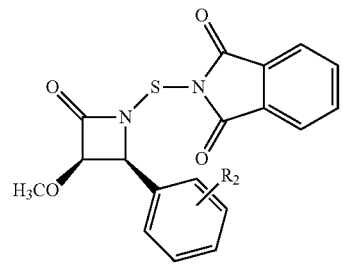

In an exemplified embodiment, a compound of the invention has the structure shown below:

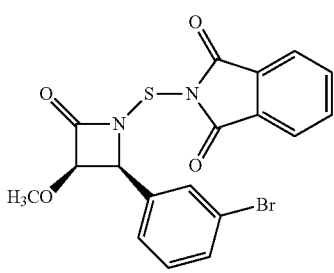 [SMILES: CO[C@H]1C(=O)N(SN2C(=O)c3ccccc3C2=O)[C@H]1c1cccc(Br)c1]

In another embodiment, a beta-lactam compound of the invention has the structure shown in formula (B):

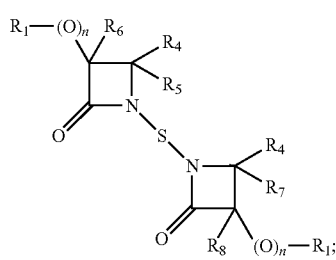

wherein $R_1$ is, independently, a hydrocarbon group having 1 to 8 carbon atoms and can be, for example, an alkyl, alkenyl, or alkynyl group; and $R_4$, $R_5$, $R_6$, $R_7$, and $R_8$ are, independently, hydrogen, alkyl, alkenyl, alkynyl, aryl, heteroalkyl, heteroaryl, cycloalkyl, heterocycloalkyl, cycloalkenyl, heterocycloalkenyl, halides, hydroxyl, nitro, cyano, alkoxy, amido, amino, carboxylic ester group, —CHO, —COOH, or COX, wherein X is Cl, F, Br, or I, any of which can be optionally substituted with $R_2$, wherein $R_2$ is one or more halides, hydroxyl, nitro, cyano, alkyl, alkenyl, alkynyl, aryl, heteroaryl, cycloalkyl, heterocycloalkyl, cycloalkenyl, heterocycloalkenyl, alkoxy, amido, amino, carboxylic ester group, —CHO, —COON, or COX, wherein X is F, Br, or I;

wherein n=0 or 1;

or a pharmaceutically acceptable salt, hydrate, ester or amide thereof.

In one embodiment, a compound of the invention has the structure shown in formula (B) wherein $R_1$ is an alkyl group. In another embodiment, $R_4$ is an aryl group. In a specific embodiment, $R_1$ is an alkyl group and $R_4$ is an aryl group. In an exemplified embodiment, $R_1$ is a methyl and $R_4$ is phenyl optionally substituted with one or more halogens. In a specific embodiment, the halogen is Cl or Br. In one embodiment, a compound has the structure:

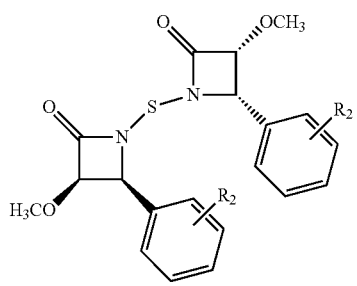

In an exemplified embodiment, a compound of the invention has the structure shown below:

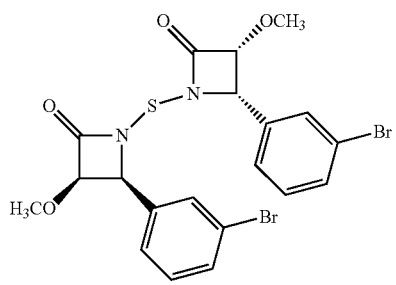 [SMILES: CO[C@H]1C(=O)N(SN2C(=O)[C@H](OC)[C@@H]2c2cccc(Br)c2)[C@H]1c1cccc(Br)c1]

In another exemplified embodiment, a compound of the invention has the structure shown below:

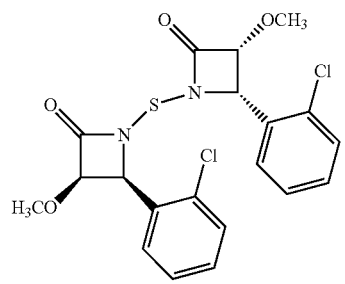 [SMILES: CO[C@H]1C(=O)N(SN2C(=O)[C@H](OC)[C@@H]2c2ccccc2Cl)[C@H]1c1ccccc1Cl]

The subject invention also concerns prodrugs of the compounds described herein. Prodrugs of compounds refers to compounds that can undergo chemical changes when provided under physiological conditions, such as when the prodrug is administered to a person or animal, to thereby convert the prodrug into an N-thiolated beta-lactam compound of the present invention.

The subject invention also concerns methods for synthesizing compounds of the invention. General reaction schemes are shown below:

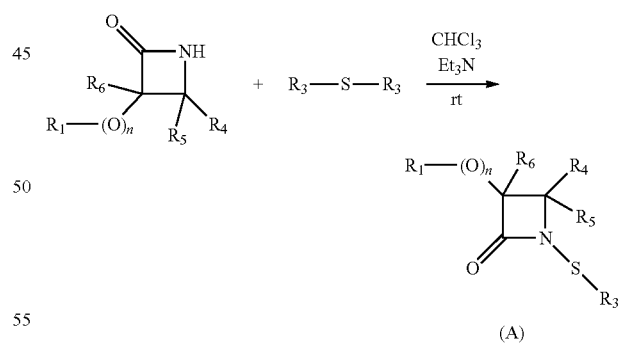

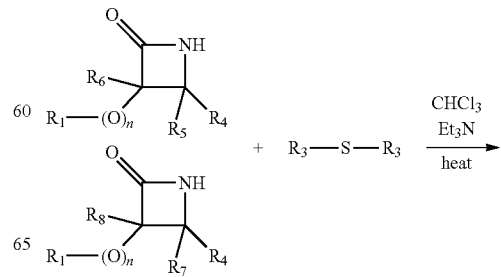

-continued

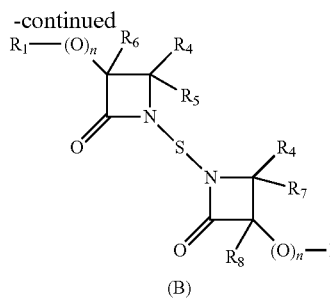

(B)

wherein R$_1$ is a hydrocarbon group having 1 to 8 carbon atoms and can be, for example, an alkyl, alkenyl, or alkynyl group;

R$_3$ is a heteroalkyl, heterocycloalkyl or heteroaryl, any of which can be optionally substituted with R$_2$, wherein R$_2$ is one or more halides, hydroxyl, nitro, cyano, alkyl, alkenyl, alkynyl, aryl, heteroaryl, cycloalkyl, heterocycloalkyl, cycloalkenyl, heterocycloalkenyl, alkoxy, amido, amino, carboxylic ester group, —CHO, —COOH, or COX, wherein X is Cl, F, Br, or I; and R$_4$, R$_5$, R$_6$, R$_7$, and R$_8$ are, independently, hydrogen, alkyl, alkenyl, alkynyl, aryl, heteroalkyl, heteroaryl, cycloalkyl, heterocycloalkyl, cycloalkenyl, heterocycloalkenyl, halides, hydroxyl, nitro, cyano, alkoxy, amido, amino, carboxylic ester group, —CHO, —COOH, or COX, wherein X is Cl, F, Br, or I, any of which can be optionally substituted with R$_2$, wherein R$_2$ is one or more halides, hydroxyl, nitro, cyano, alkyl, alkenyl, alkynyl, aryl, heteroaryl, cycloalkyl, heterocycloalkyl, cycloalkenyl, heterocycloalkenyl, alkoxy, amido, amino, carboxylic ester group, —CHO, —COOH, or COX, wherein X is Cl, F, Br, or I;

wherein n=0 or 1;

or a pharmaceutically acceptable salt, hydrate, ester or amide thereof.

Figure 3A:
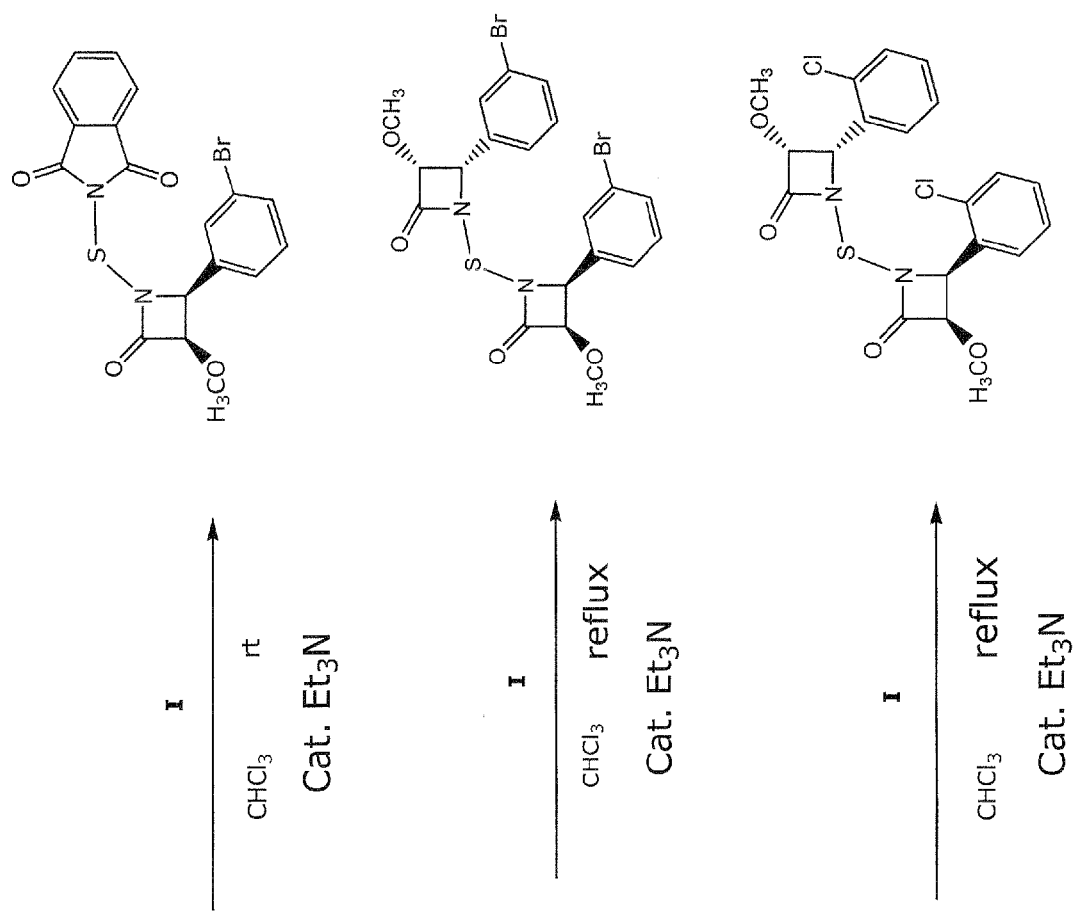
FIGS. 3A-3C show reaction schemes for the synthesis of heterosubstituted N-thiolated beta-lactam compounds of the present invention.
Figure 3A:
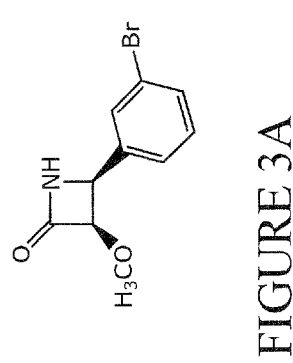
Figure 3B:
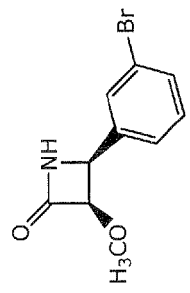
Figure 3C:
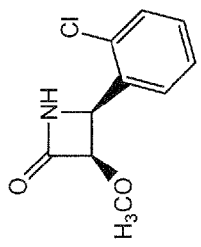
Figure 4A:
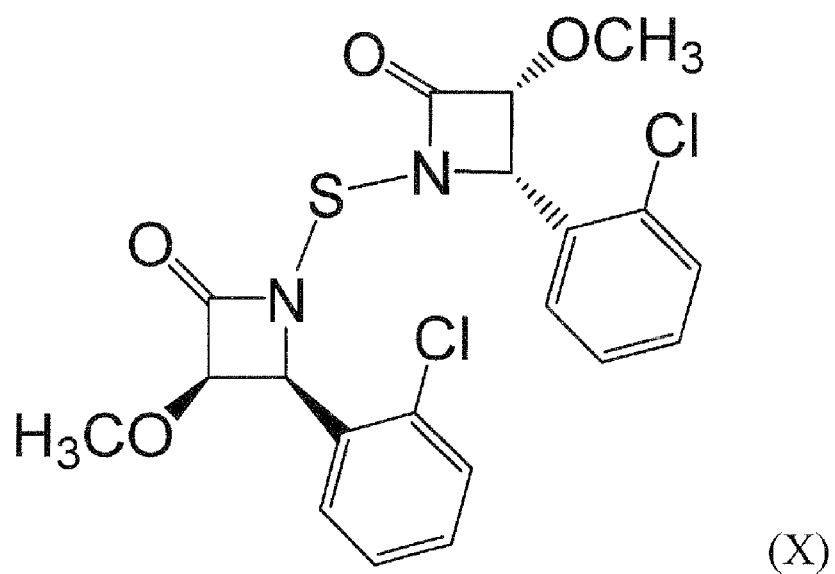
FIGS. 4A-4C show examples of heterosubstituted N-thiolated beta-lactam compounds of the present invention identified as compounds.
Figure 4B:
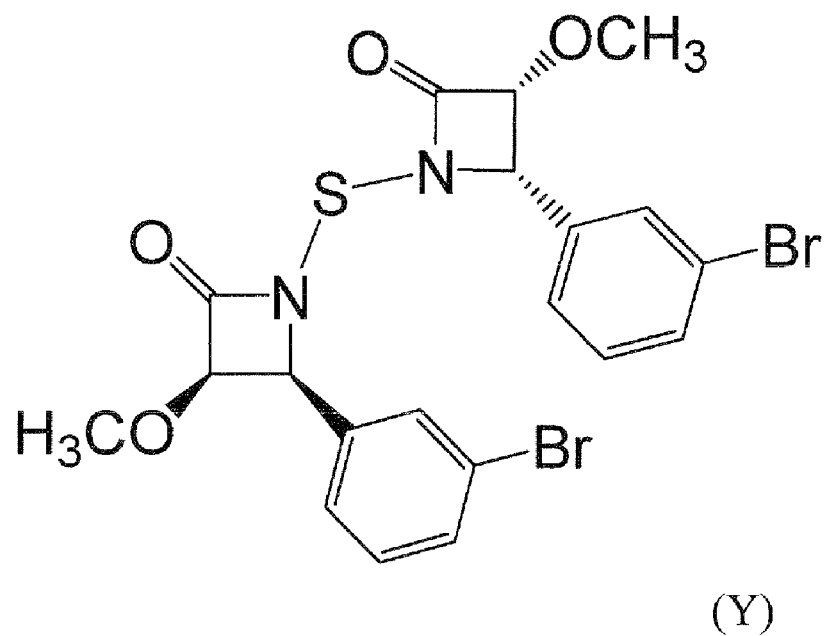
Figure 4C:
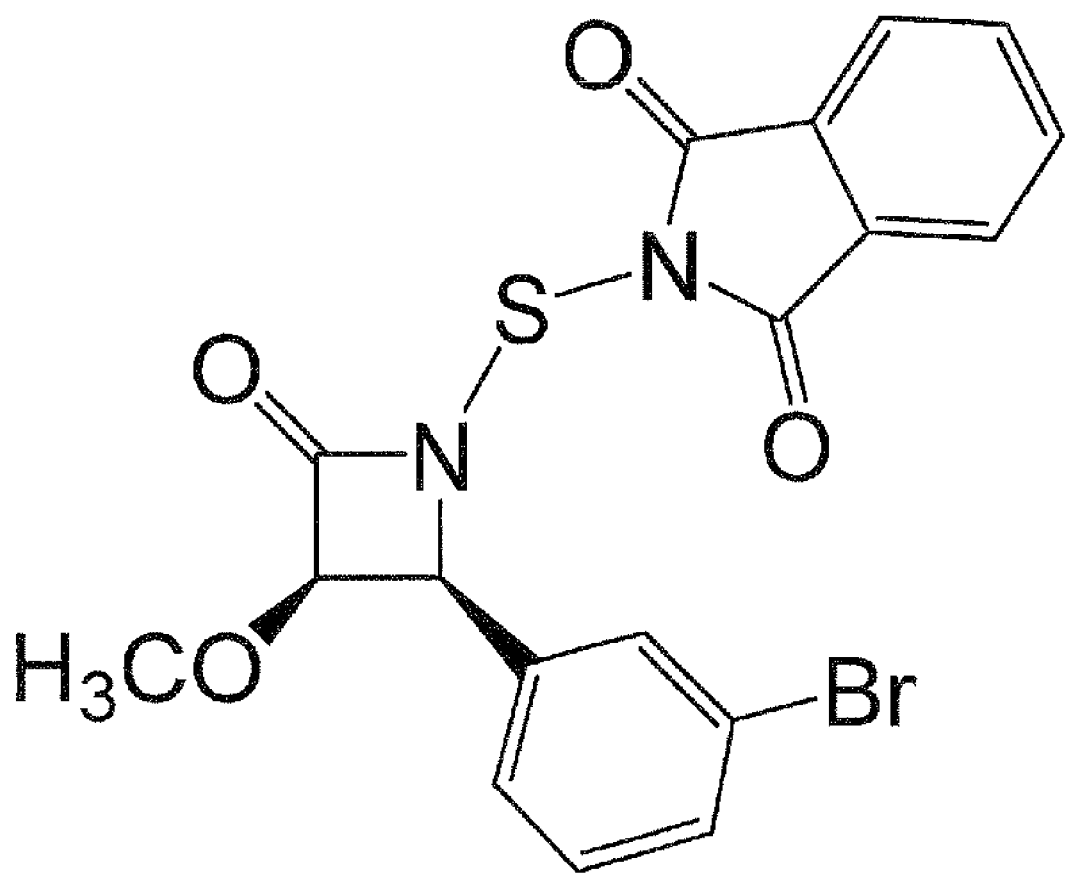
Figure 5:
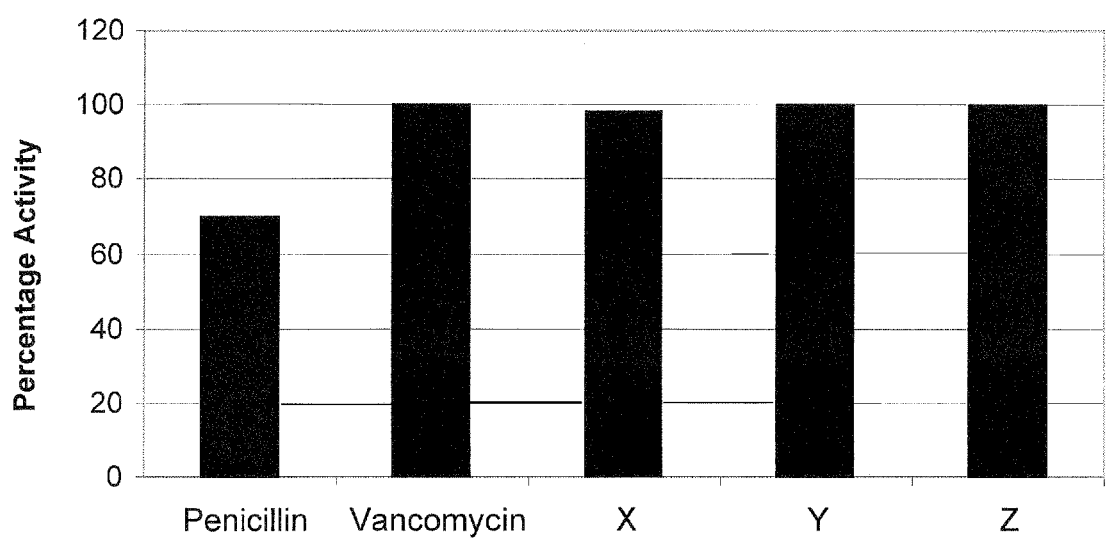
FIG. 5 shows bioactivity of heterosubstituted N-thiolated beta-lactam compounds X, Y, and Z (shown in FIG. 4) of the present invention as tested in Kirby-Bauer diffusion assay against methicillin resistant *Staphylococcus aureus*.

Beta-lactam starting material can be synthesized as described in Turos et al. (2005). In one embodiment, a beta-lactam starting material is reacted with phthalimide dimer in a solvent, such as chloroform (CHCl$_3$), and triethylamine (Et$_3$N) under room temperature conditions or reflux (heat) conditions at elevated temperature. Phthalimide dimer can be synthesized as described in Kalnins (1966). Chemical reactions and products are shown in FIGS. 3A-3C. Methods of synthesis related to N-thiolated beta-lactam are also disclosed in U.S. Pat. Nos. 6,476,015 and 6,946,458.

The subject invention also concerns methods of using one or more compounds of the invention to treat or prevent a bacterial infection. In one embodiment, a method of the invention comprises administering an effective amount of one or more compounds of the invention to a person or animal in need of treatment. Optionally, the subject methods provide for screening of persons or animals to determine whether the person or animal has a bacterial infection amenable to treatment by a compound of the present invention. Patients that can be treated according to the present invention, include, but are not limited to, humans and other mammals (such as primates (monkey, chimpanzee, ape, etc.) dog, cat, cow, pig, horse, etc.), or bird, reptile, etc. Compounds and pharmaceutically acceptable compositions administered to the person or animal via any suitable route, including, for example, orally or parenterally, by intravenous, intramuscular, intraperitoneally, subcutaneous or topical routes, or via nasal or rectal administration. An ordinarily skilled clinician can readily assess the patient to determine optimal dosage, dosage form, and dosage schedule for the patient.

Bacterial infections that can be treated or prevented include, but are not limited to, infections caused by gram-positive bacteria, such as *Bacillus* spp., *Listeria* spp., *Staphylococcus* spp., *Streptococcus* spp., *Enterococcus* spp., and *Clostridium* spp., and gram-negative bacteria, such as *Escherichia* spp., *Salmonella* spp., *Pseudomonas* spp., *Heliobacter* app., *Legionella* spp., *Moraxella* spp., *Neisseria* spp., *Hemophilus* spp., *Klebsiella* spp. and *Enterobacter* spp. Other bacteria that can be inhibited or killed by compounds of the invention include *Shigella* spp., *Acromonas* spp., *Vibrio* spp., *Bordatella* spp., *Brucella* spp., *Treponema* spp., *Leptospira* spp., *Corynebacter* spp., *Micrococcus* spp., *Streptomyces* spp., *Nocardia* spp., *Actinomyces* spp., *Yersinia* spp., *Chlamydia* spp., *Mycoplasma* spp., *Rickettsiae* spp., *Pasteurella* spp., *Spirillum* spp., and *Mycobacterium* spp. In one embodiment, a person or animal being treated according to the methods herein is infected with methicillin-resistant *Staphylococcus aureus*. In one embodiment, a compound of the invention is provided as a pharmaceutically acceptable composition that comprises, for example, a pharmaceutically acceptable carrier or excipient.

The bioactivity of these compounds has been tested by Kirby-Bauer diffusion assay against methicillin resistant *Staphylococcus aureus* (MRSA) and were found to have antibacterial activity against the MRSA equal to that of Vancomycin. For example, the compounds of the invention can be administered to humans or animals to inhibit the growth of bacteria, such as *Staphylococcus*, including MRSA. The mode of action of these compounds is believed to be similar to N-thiolated beta-lactams and they may be formulated and used in a similar fashion (see U.S. Pat. No. 6,946,458 (Turos) and U.S. Pat. No. 6,476,015 (Turos et al.), which are incorporated herein by reference in their entirety).

The subject invention also concerns methods for killing or inhibiting the growth of a bacterial organism. In one embodiment, a bacterial organism is contacted with one or more compounds of the present invention. Bacterial organisms contemplated within the scope of the invention include gram-positive bacteria, such as *Bacillus* spp., *Listeria* spp., *Staphylococcus* spp., *Streptococcus* spp., *Enterococcus* spp., and *Clostridium* spp., and gram-negative bacteria, such as *Escherichia* spp., *Salmonella* spp., *Pseudomonas* spp., *Heliobacter* app., *Legionella* spp., *Moraxella* spp., *Neisseria* spp., *Hemophilus* spp., *Klebsiella* spp. and *Enterobacter* spp. Other bacteria that can be inhibited or killed by compounds of the invention include *Shigella* ssp., *Acromonas* spp., *Vibrio* spp., *Bordatella* spp., *Brucella* spp., *Treponema* spp., *Leptospira* spp., *Corynebacter* spp., *Micrococcus* spp., *Streptomyces* spp., *Nocardia* spp., *Actinomyces* spp., *Yersinia* spp., *Chlamydia* spp., *Mycoplasma* spp., *Rickettsiae* spp., *Pasteurella* spp., *Spirillum* spp., and *Mycobacterium* spp. In an exemplified embodiment, the bacterial organism is a methicillin-resistant strain of *Staphylococcus aureus*.

The compounds and compositions of the invention can also be formulated for feeding livestock and the use thereof is contemplated by the present invention.

The invention further encompasses methods for inhibiting the growth of bacteria by contacting the bacteria with an effective amount of the compounds of the invention in vitro or in vivo, or by applying the compound to a substrate (surface) likely to come in contact with the bacteria, such as a work surface, table, surgical instrument, implant or other device to be placed in or on the body (i.e., foreign object to be inserted into a subject, such as a stent, catheter, access port, intravenous delivery tube (Hickman), heart valve, dental implant, electro-mechanical device, prosthetic device, glucose sensor, or stabilizing device such as orthopedic nails and pins), eating or cooking utensil, etc. The subject invention also concerns substrates which have a compound of the invention attached or applied thereto.

As used herein, alkyl means straight or branched chain, saturated or mono- or polyunsaturated hydrocarbon groups having from 1 to 20 carbon atoms and $C_{1-x}$ alkyl means straight or branched chain alkyl groups containing from one up to X carbon atoms. For example, $C_{1-6}$ alkyl means straight or branched chain alkyl groups containing from one up to 6 carbon atoms. Alkoxy means an alkyl-O— group in which the alkyl group is as previously described. Cycloalkyl includes a nonaromatic monocyclic or multicyclic ring system, including fused and spiro rings, of from about three to about 10 carbon atoms. A cyclic alkyl may optionally be partially unsaturated. Cycloalkoxy means a cycloalkyl-O-group in which cycloalkyl is as defined herein. Aryl means an aromatic monocyclic or multicyclic carbocyclic ring system, including fused and spiro rings, containing from about six to about 14 carbon atoms. Aryloxy means an aryl-O— group in which the aryl group is as described herein. Alkylcarbonyl means a RC(O)— group where R is an alkyl group as previously described. Alkoxycarbonyl means an ROC(O)— group where R is an alkyl group as previously described. Cycloalkylcarbonyl means an RC(O)— group where R is a cycloalkyl group as previously described. Cycloalkoxycarbonyl means an ROC(O)— group where R is a cycloalkyl group as previously described.

Heteroalkyl means a straight or branched-chain having from one to 20 carbon atoms and one or more heteroatoms selected from nitrogen, oxygen, sulfur, or silicon, wherein the nitrogen and sulfur atoms may optionally be oxidized, i.e., in the form of an N-oxide or an S-oxide. Heterocycloalkyl means a monocyclic or multicyclic ring system (which may be saturated or partially unsaturated), including fused and Spiro rings, of about five to about 14 elements wherein one or more of the elements in the ring system is an element other than carbon and is selected from nitrogen, oxygen, silicon, or sulfur atoms. Heteroaryl means a five to about a 14-membered aromatic monocyclic or multicyclic hydrocarbon ring system, including fused and spiro rings, in which one or more of the elements in the ring system is an element other than carbon and is selected from nitrogen, oxygen, silicon, or sulfur and wherein an N atom may be in the form of an N-oxide. Arylcarbonyl means an aryl-CO— group in which the aryl group is as described herein. Heteroarylcarbonyl means a heteroaryl-CO— group in which the heteroaryl group is as described herein and heterocycloalkylcarbonyl means a heterocycloalkyl-CO— group in which the heterocycloalkyl group is as described herein. Aryloxycarbonyl means an ROC(O)— group where R is an aryl group as previously described. Heteroaryloxycarbonyl means an ROC(O)— group where R is a heteroaryl group as previously described. Heterocycloalkoxy means a heterocycloalkyl-O— group in which the heterocycloalkyl group is as previously described. Heterocycloalkoxycarbonyl means an ROC(O)— group where R is a heterocycloalkyl group as previously described.

Examples of saturated alkyl groups include, but are not limited to, methyl, ethyl, N-propyl, isopropyl, N-butyl, tert-butyl, isobutyl, sec-butyl, N-pentyl, N-hexyl, N-heptyl, and N-octyl. An unsaturated alkyl group is one having one or more double or triple bonds. Unsaturated alkyl groups include, for example, ethenyl, propenyl, butenyl, hexenyl, vinyl, 2-propenyl, 2-isopentenyl, 2-butadienyl, ethynyl, 1-propynyl, 3-propynyl, 3-butynyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl; 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, 11-dodecenyl, 1-tridecenyl, 2-tridecenyl, 3-tridecenyl, 4-tridecenyl, 5-tridecenyl, 6-tridecenyl, 7-tridecenyl, 8-tridecenyl, 9-tridecenyl, 10-tridecenyl, 11-tridecenyl, 12-tridecenyl, 1-tetradecenyl, 2-tetradecenyl, 3-tetradecenyl, 4-tetradecenyl, 5-tetradecenyl, 6-tetradecenyl, 7-tetradecenyl, 8-tetradecenyl, 9-tetradecenyl, 10-tetradecenyl, 11-tetradecenyl, 12-tetradecenyl, 13-tetradecenyl, 1-pentadecenyl, 2-pentadecenyl, 3-pentadecenyl, 4-pentadecenyl, 5-pentadecenyl, 6-pentadecenyl, 7-pentadecenyl, 8-pentadecenyl, 9-pentadecenyl, 10-pentadecenyl, 11-pentadecenyl, 12-pentadecenyl, 13-pentadecenyl, and 14-pentadecenyl. Cycloalkyl groups include, for example, cyclopropyl, cyclobutyl, cyclopentyl, cyclohexyl, 1-cyclohexenyl, 3-cyclohexenyl, cycloheptyl, and cyclooctyl. Heterocycloalkyl groups include, for example, 1-piperidinyl, 2-piperidinyl, 3-piperidinyl, 3-morpholinyl, 4-morpholinyl, tetrahydrofuran-2-yl, tetrahydrofuran-3-yl, tetrahydrothien-2-yl, tetrahydrothien-3-yl, 1-piperazinyl, 2-piperazinyl, 1,4-diazabicyclooctane, and succinimido. Aryl groups include, for example, phenyl, indenyl, biphenyl, 1-naphthyl, 2-naphthyl, anthracenyl, and phenanthracenyl. Heteroaryl groups include, for example, 1-pyrrolyl, 2-pyrrolyl, 3-pyrrolyl, furyl, thienyl, imidazolyl, oxazolyl, thiazolyl, pyrazolyl, pyridyl, indolyl, quinolinyl, isoquinolinyl, benzoquinolinyl, carbazolyl, phthalimido, pyrimidinyl, terazolyl, and diazaphenanthrenyl. "Alkoxy" can include methoxy, ethoxy, propoxy, isopropoxy, butoxy, iso-butoxy, sec-butoxy, pentoxy, 3-pentoxy, hexoxy, heptyloxy, octyloxy, nonyloxy, decyloxy, undecyloxy, dodecyloxy, tridecyloxy, tetradecyloxy, or pentadecyloxy.

As used herein, halogen means the elements fluorine (F), chlorine (Cl), Bromine (Br), and iodine (I).

Compounds of the subject invention also include hydrates and physiologically-acceptable salts of the subject compounds. Physiologically-acceptable salts includes salts of the compounds of the invention which are prepared with acids or bases, depending on the particular substituents found on the subject compounds described herein. Examples of physiologically-acceptable base addition salts include sodium, potassium, calcium, ammonium, or magnesium salt. Examples of physiologically-acceptable acid addition salts include hydrochloric, hydrobromic, nitric, phosphoric, carbonic, sulfuric, and organic acids like acetic, propionic, benzoic, succinic, fumaric, mandelic, oxalic, citric, tartaric, maleic, and the like. Physiologically-acceptable salts of compounds of the invention can be prepared using conventional techniques.

It will be appreciated by those skilled in the art that compounds of the invention may contain one or more asymmetrically substituted carbon atoms which can give rise to stereoisomers. It is understood that the invention extends to all such stereoisomers, including enantiomers, and diastereoisomers and mixtures, including racemic mixtures thereof.

Compounds of the subject invention can be formulated according to known methods for preparing physiologically acceptable compositions. Formulations are described in detail in a number of sources which are well known and readily available to those skilled in the art. For example, *Remington's Pharmaceutical Science* by F. W. Martin describes formulations which can be used in connection with the subject invention. In general, the compositions of the subject invention will be formulated such that an effective amount of the compound is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional physiologically-acceptable carriers and diluents which are known to those skilled in the art. Examples of carriers or diluents for use with the subject compounds include water, saline, ethanol, dimethyl sulfoxide, glycerol, alumina, starch, and equivalent carriers and diluents. To provide for the administration of such dosages for the desired therapeutic treatment, compositions of the invention will advantageously comprise between about 0.1% and 99%, and especially, 1 and 15% by weight of the total of one or more of the subject compounds based on the weight of the total composition including carrier or diluent.

In addition, the compounds of the present invention that exhibit antibacterial activity may also be used as medicaments, and also as substances for preserving inorganic and organic materials, especially organic materials of all kinds, for example, polymers, lubricants, paints, fibers, leather, paper, timber, foodstuffs, and water. For example, these compounds can be covalently bonded to the polymer.

The subject invention also concerns a kit comprising in one or more containers at least one compound of the subject invention. In one embodiment, a kit of the invention also comprises a pharmaceutically acceptable diluent and/or carrier. A kit of the invention can also comprise, in addition to at least one compound of the present invention, other antibiotics, such as penicillin, cephalosporins, carbapenems, and beta-lactamase inhibitors.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

U.S. Pat. No. 6,946,458
U.S. Pat. No. 6,476,015
Kalnins, Malda (1966) "Reactions of Phthalimide and Potassium Phthalimide with Sulfur Monochloride," *Canadian Journal of Chemistry*, 44: 2111-2113.
Morin et al. (1982) "Chemistry and Biology of beta-lactam Antibiotics," Vol. 1-3. New York: Academic Press.
Kukacs et al. (1990) "Recent Progress in the Chemical Synthesis of Antibiotics" Berlin, Springer-Verlag.
Turos, E. et al. (2005) "N-Methylthio β-lactam Antibacterials: Effects of the $C_3/C_4$ Ring Substituents on Anti-MRSA Activity," *Bioorganic $ Medicinal Chemistry*, 13: 6289-6308.
Turos et al. (2000) *Tetrahedron* 56:5571-5578.
Ren et al. (1998) *J. Org. Chem.* 63: 8898-8917.

We claim:

1. A compound having the structure shown in formula (B):

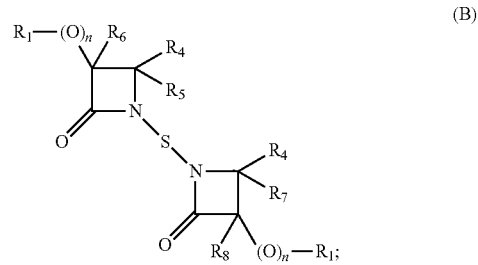

wherein $R_1$ is a hydrocarbon group having 1 to 8 carbon atoms; and wherein $R_4$, $R_5$, $R_6$, $R_7$, and $R_8$ are, independently, hydrogen, alkyl, alkenyl, alkynyl, aryl, heteroalkyl, heteroaryl, cycloalkyl, heterocycloalkyl, cycloalkenyl, heterocycloalkenyl, halogen, hydroxyl, nitro, cyano, alkoxy, amido, amino, —CHO, —COOH, or COX, wherein X is Cl, F, Br, or I, any of which can be optionally substituted with $R_2$, wherein $R_2$ is one or more halogen, hydroxyl, nitro, cyano, alkyl, alkenyl, alkynyl, aryl, heteroaryl, cycloalkyl, heterocycloalkyl, cycloalkenyl, heterocycloalkenyl, alkoxy, amido, amino, —CHO, —COOH, or COX, wherein X is Cl, F, Br, or I; and wherein n=0 or 1;

or a pharmaceutically acceptable salt thereof.

2. The compound according to claim 1, wherein $R_1$ is alkyl.

3. The compound according to claim 1, wherein $R_4$ is aryl.

4. The compound according to claim 1, wherein $R_1$ is alkyl and $R_4$ is aryl.

5. The compound according to claim 1, wherein $R_1$ is methyl and $R_4$ is phenyl optionally substituted with one or more halogen.

6. The compound according to claim 5, wherein said one or more halogen are selected from the group consisting of Cl and Br.

7. A composition comprising a compound having the structure shown in formula (B)

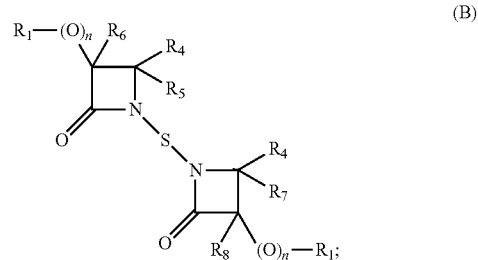

wherein $R_1$ is a hydrocarbon group having 1 to 8 carbon atoms; and wherein R₄, R₅, R₆, R₇, and R₈ are, independently, hydrogen, alkyl, alkenyl, alkynyl, aryl, heteroalkyl, heteroaryl, cycloalkyl, heterocycloalkyl, cycloalkenyl, heterocycloalkenyl, halogen, hydroxyl, nitro, cyano, alkoxy, amido, amino, —CHO, —COOH, or COX, wherein X is Cl, F, Br, or I, any of which can be optionally substituted with R₂, wherein R₂ is one or more halogen, hydroxyl, nitro, cyano, alkyl, alkenyl, alkynyl, aryl, heteroaryl, cycloalkyl, heterocycloalkyl, cycloalkenyl, heterocycloalkenyl, alkoxy, amido, amino, —CHO, —COOH, or COX, wherein X is Cl, F, Br, or I;

wherein n=0 or 1;

or a pharmaceutically acceptable salt, hydrate, ester or amide thereof;

and a pharmaceutically acceptable carrier, diluent, or excipient.

8. A method for treating or preventing a bacterial infection in a person or animal, said method comprising administering an effective amount of a compound, or a composition comprising said compound, to said person or animal, wherein said compound has the structure shown in formula (B):

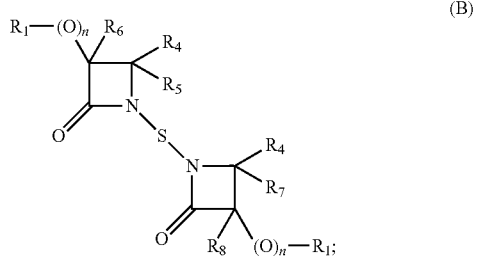

(B)

wherein R₁ is a hydrocarbon group having 1 to 8 carbon atoms; and wherein R₄, R₅, R₆, R₇, and R₈ are, independently, hydrogen, alkyl, alkenyl, alkynyl, aryl, heteroalkyl, heteroaryl, cycloalkyl, heterocycloalkyl, cycloalkenyl, heterocycloalkenyl, halogen, hydroxyl, nitro, cyano, alkoxy, amido, amino, —CHO, —COOH, or COX, wherein X is Cl, F, Br, or I, any of which can be optionally substituted with R₂, wherein R₂ is one or more halogen, hydroxyl, nitro, cyano, alkyl, alkenyl, alkynyl, aryl, heteroaryl, cycloalkyl, heterocycloalkyl, cycloalkenyl, heterocycloalkenyl, alkoxy, amido, amino, —CHO, —COOH, or COX, wherein X is Cl, F, Br, or I; and wherein n=0 or 1;

or a pharmaceutically acceptable salt, hydrate, ester or amide thereof.

9. The method according to claim 8, wherein R₁ is alkyl.

10. The method according to claim 8, wherein R₄ is aryl.

11. The method according to claim 8, wherein R₁ is alkyl and R₄ is aryl.

12. The method according to claim 8, wherein R₁ is methyl and R₄ is phenyl optionally substituted with one or more halogen.

13. The method according to claim 12, wherein said one or more halogen are selected from the group consisting of Cl and Br.

14. The method according to claim 8, wherein the compound has the structure:

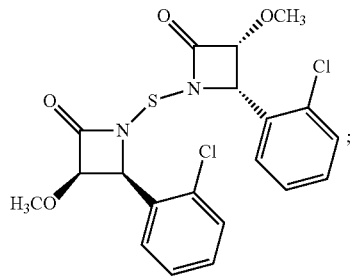 [SMILES: CO[C@H]1C(=O)N(SN2C(=O)[C@H](OC)[C@@H]2c2ccccc2Cl)[C@H]1c1ccccc1Cl]

or a pharmaceutically acceptable salt or hydrate thereof.

15. The method according to claim 8, wherein the compound has the structure:

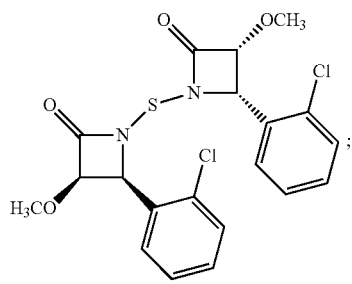 [SMILES: CO[C@H]1C(=O)N(SN2C(=O)[C@H](OC)[C@@H]2c2ccccc2Cl)[C@H]1c1ccccc1Cl]

or a pharmaceutically acceptable salt or hydrate thereof.

16. The method according to claim 8, wherein said animal is a primate, dog, cat, cow, pig, or horse.

17. The method according to claim 8, wherein said bacterial infection is caused by one of the following bacteria: *Bacillus* spp., *Listeria* spp., *Staphylococcus* spp., *Streptococcus* spp., *Enterococcus* spp., *Clostridium* spp., *Escherichia* spp., *Salmonella* spp., *Pseudomonas* spp., *Heliobacter* spp., *Legionella* spp., *Moraxella* spp., *Neisseria* spp., *Hemophilus* spp., *Klebsiella* spp., *Enterobacter* spp., *Shigella* spp., *Acromonas* spp., *Vibrio* spp., *Bordatella* spp., *Brucella* spp., *Treponema* spp., *Leptospira* spp., *Corynebacter* spp., *Micrococcus* spp., *Streptomyces* spp., *Nocardia* spp., *Actinomyces* spp., *Yersinia* spp., *Chlamydia* spp., *Mycoplasma* spp., *Rickettsiae* spp., *Pasteurella* spp., *Spirillum* spp., or *Mycobacterium* spp.

18. The method according to claim 8, wherein said bacterial infection is caused by a methicillin resistant strain of *Staphylococcus aureus*.

19. The method according to claim 8, wherein said compound or composition is administered to said person or animal via an oral, parenteral, nasal, or rectal route of administration.

20. The method according to claim 8, wherein said composition comprises a pharmaceutically acceptable carrier, diluent, or excipient.

21. A method for treating or preventing a bacterial infection in a person or animal, said method comprising administering an effective amount of a compound, or a composition comprising said compound, to said person or animal, wherein said compound has the structure shown in formula (A):

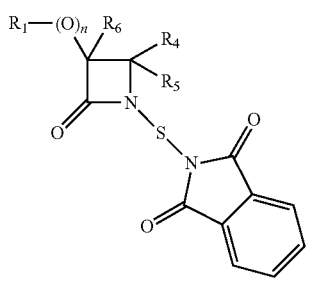

wherein R₁ is a hydrocarbon group having 1 to 8 carbon atoms;

R₄, R₅, and R₆ are, independently, hydrogen, alkyl, alkenyl, alkynyl, aryl, heteroalkyl, heteroaryl, cycloalkyl, heterocycloalkyl, cycloalkenyl, heterocycloalkenyl, halogen, hydroxyl, nitro, cyano, alkoxy, amido, amino, —CHO, —COOH, or COX, wherein X is Cl, F, Br, or I; any of which can be optionally substituted with R₂, wherein R₂ is one or more halogen, hydroxyl, nitro, cyano, alkyl, alkenyl, alkynyl, aryl, heteroaryl, cycloalkyl, heterocycloalkyl, cycloalkenyl, heterocycloalkenyl, alkoxy, amido, amino, —CHO, —COOH, or COX, wherein X is Cl, F, Br, or I; and wherein n=0 or 1;

or a pharmaceutically acceptable salt, hydrate, ester or amide thereof.

22. The method according to claim 21, wherein R₁ is alkyl.

23. The method according to claim 21, wherein R₄ is aryl.

24. The method according to claim 21, wherein R₁ is alkyl and R₄ is aryl.

25. The method according to claim 21, wherein R₁ is methyl and R₄ is phenyl optionally substituted with one or more halogen.

26. The method according to claim 25, wherein said one or more are selected from the group consisting of Cl and Br.

27. The method according to claim 21, wherein the compound has the structure:

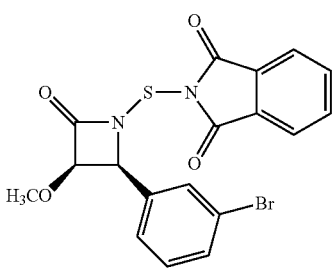 [SMILES: CO[C@H]1C(=O)N(SN2C(=O)c3ccccc3C2=O)[C@H]1c1cccc(Br)c1]

or a pharmaceutically acceptable salt or hydrate thereof.

28. The method according to claim 21, wherein said animal is a primate, dog, cat, cow, pig, or horse.

29. The method according to claim 21, wherein said bacterial infection is caused by one of the following bacteria: *Bacillus* spp., *Listeria* spp., *Staphylococcus* spp., *Streptococcus* spp., *Enterococcus* spp., *Clostridium* spp., *Escherichia* spp., *Salmonella* spp., *Pseudomonas* spp., *Heliobacter* spp., *Legionella* spp., *Moraxella* spp., *Neisseria* spp., *Hemophilus* spp., *Klebsiella* spp., *Enterobacter* spp., *Shigella* spp., *Aeromonas* spp., *Vibrio* spp., *Bordatella* spp., *Brucella* spp., *Treponema* spp., *Leptospira* spp., *Corynebacter* spp., *Micrococcus* spp., *Streptomyces* spp., *Nocardia* spp., *Actinomyces* spp., *Yersinia* spp., *Chlamydia* spp., *Mycoplasma* spp., *Rickettsiae* spp., *Pasteurella* spp., *Spirillum* spp., or *Mycobacterium* spp.

30. The method according to claim 21, wherein said bacterial infection is caused by a methicillin resistant strain of *Staphylococcus aureus*.

31. The method according to claim 21, wherein said compound or composition is administered to said person or animal via an oral, parenteral, nasal, or rectal route of administration.

32. The method according to claim 21, wherein said composition comprises a pharmaceutically acceptable carrier, diluent, or excipient.

33. A method for treating or preventing a bacterial infection in a person or animal, said method comprising administering an effective amount of a compound, or a composition comprising said compound, to said person or animal, wherein said compound has the structure shown in formula (C):

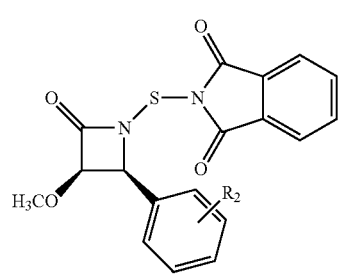

wherein R₂ is one or more halogen, hydroxyl, nitro, cyano, alkyl, alkenyl, alkynyl, aryl, heteroaryl, cycloalkyl, heterocycloalkyl, cycloalkenyl, heterocycloalkenyl, alkoxy, amino, amino, —CHO, —COON, or COX, wherein X is Cl, F, Br, or I;

or a pharmaceutically acceptable salt or hydrate thereof.

34. The method according to claim 33, wherein R₂ is one or more halogen.

35. The method according to claim 34, wherein said one or more halogen is selected from the group consisting of Cl and Br.

36. The method according to claim 33, wherein said animal is a primate, dog, cat, cow, pig, or horse.

37. The method according to claim 33, wherein said bacterial infection is caused by one of the following bacteria: *Bacillus* spp., *Listeria* spp., *Staphylococcus* spp., *Streptococcus* spp., *Enterococcus* spp., *Clostridium* spp., *Escherichia* spp., *Salmonella* spp., *Pseudomonas* spp., *Heliobacter* spp., *Legionella* spp., *Moraxella* spp., *Neisseria* spp., *Hemophilus* spp., *Klebsiella* spp., *Enterobacter* spp., *Shigella* spp., *Aeromonas* spp., *Vibrio* spp., *Bordatella* spp., *Brucella* spp., *Treponema* spp., *Leptospira* spp., *Corynebacter* spp., *Micrococcus* spp., *Streptomyces* spp., *Nocardia* spp., *Actinomyces* spp., *Yersinia* spp., *Chlamydia* spp., *Mycoplasma* spp., *Rickettsiae* spp., *Pasteurella* spp., *Spirillum* spp., or *Mycobacterium* spp.

38. The method according to claim 33, wherein said bacterial infection is caused by a methicillin resistant strain of *Staphylococcus aureus*.

39. The method according to claim 33, wherein said compound or composition is administered to said person or animal via an oral, parenteral, nasal, or rectal route of administration.

40. The method according to claim 33, wherein said composition comprises a pharmaceutically acceptable carrier, diluent, or excipient.

41. The compound of claim 1, wherein the salt is a sodium, potassium, calcium, ammonium, magnesium, hydrochloric, hydrobromic, nitric, phosphoric, carbonic, sulfuric, acetic acid, propionic acid, benzoic acid, succinic acid, fumaric acid, mandelic acid, oxalic acid, citric acid, tartaric acid, or maleic acid salt.

42. The composition of claim 7, wherein the salt is a sodium, potassium, calcium, ammonium, magnesium, hydrochloric, hydrobromic, nitric, phosphoric, carbonic, sulfuric, acetic acid, propionic acid, benzoic acid, succinic acid, fumaric acid, mandelic acid, oxalic acid, citric acid, tartaric acid, or maleic acid salt.

43. The method of claim 8, wherein the salt is a sodium, potassium, calcium, ammonium, magnesium, hydrochloric, hydrobromic, nitric, phosphoric, carbonic, sulfuric, acetic acid, propionic acid, benzoic acid, succinic acid, fumaric acid, mandelic acid, oxalic acid, citric acid, tartaric acid, or maleic acid salt.

44. The method of claim 21, wherein the salt is a sodium, potassium, calcium, ammonium, magnesium, hydrochloric, hydrobromic, nitric, phosphoric, carbonic, sulfuric, acetic acid, propionic acid, benzoic acid, succinic acid, fumaric acid, mandelic acid, oxalic acid, citric acid, tartaric acid, or maleic acid salt.

45. The method of claim 33, wherein the salt is a sodium, potassium, calcium, ammonium, magnesium, hydrochloric, hydrobromic, nitric, phosphoric, carbonic, sulfuric, acetic acid, propionic acid, benzoic acid, succinic acid, fumaric acid, mandelic acid, oxalic acid, citric acid, tartaric acid, or maleic acid salt.

* * * * *

UNITED STATES PATENT AND TRADEMARK OFFICE
CERTIFICATE OF CORRECTION

PATENT NO. : 8,404,671 B2
APPLICATION NO. : 12/951778
DATED : March 26, 2013
INVENTOR(S) : Edward Turos and Praveen Ramaraju It is certified that error appears in the above-identified patent and that said Letters Patent is hereby corrected as shown below:

In the Specifications:

Column 3,
Line 41, "-COON, or" should read -- -COOH, or--.
Line 42, "X is F, BR, or I" should read --X is Cl, F, Br, or I--.

Column 7,
Line 35, "Spiro rings" should read --spiro rings--.

Column 8,
Line 67, "by F. W." should read --by E. W.--.

Column 12,
Lines 5-15,

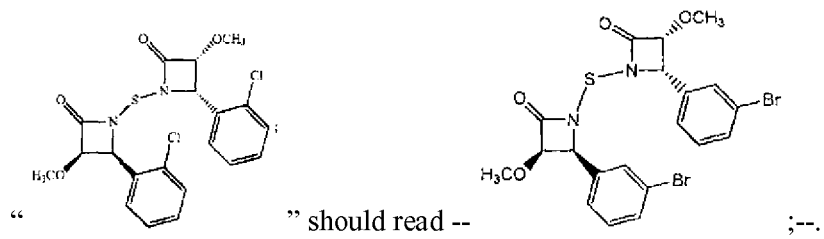

" should read -- ;--.

Column 13,
Lines 64-65, "*Aeromonas* spp.," should read --*Acromonas* spp.,--.

Column 14,
Line 37, "amino, amino" should read --amido, amino--.
Line 37, "-COON," should read -- -COOH,--.
Lines 54-55, "*Aeromonas* spp. ," should read --*Acromonas* spp.,"--.

Signed and Sealed this
Sixteenth Day of July, 2013

Teresa Stanek Rea
*Acting Director of the United States Patent and Trademark Office*